United States Patent
Lincoln et al.

(10) Patent No.: US 6,963,777 B2
(45) Date of Patent: Nov. 8, 2005

(54) CARDIAC RHYTHM MANAGEMENT SYSTEM AND METHOD USING TIME BETWEEN MITRAL VALVE CLOSURE AND AORTIC EJECTION

(75) Inventors: William C. Lincoln, Coon Rapids, MN (US); Gerrard M. Carlson, Champlin, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 510 days.

(21) Appl. No.: 10/099,865

(22) Filed: Mar. 13, 2002

(65) Prior Publication Data

US 2003/0176896 A1 Sep. 18, 2003

(51) Int. Cl.[7] .............................................. A61N 1/362
(52) U.S. Cl. ....................................................... 607/18
(58) Field of Search ..................................... 607/1–156

(56) References Cited

U.S. PATENT DOCUMENTS

| | | | |
|---|---|---|---|
| 5,168,869 A | 12/1992 | Chirife .................. | 128/419 PG |
| 5,334,222 A | 8/1994 | Salo et al. ..................... | 607/17 |
| 5,454,838 A * | 10/1995 | Vallana et al. ................ | 607/19 |
| 5,540,727 A | 7/1996 | Tockman et al. ............. | 607/18 |
| 5,549,650 A | 8/1996 | Bornzin et al. ............... | 607/24 |
| 5,554,177 A | 9/1996 | Kieval et al. ................. | 607/17 |
| 5,562,711 A | 10/1996 | Yerich et al. ................. | 607/17 |
| 5,578,064 A | 11/1996 | Prutchi ......................... | 607/19 |
| 5,584,868 A | 12/1996 | Salo et al. ..................... | 607/17 |
| 5,609,612 A | 3/1997 | Plicchi et al. ................. | 607/17 |
| 5,628,777 A | 5/1997 | Moberg et al. ............. | 607/122 |
| 5,674,256 A | 10/1997 | Carlson ........................ | 607/17 |
| 5,700,283 A | 12/1997 | Salo ............................. | 607/17 |
| 5,800,471 A | 9/1998 | Baumann ..................... | 607/25 |
| 5,836,987 A | 11/1998 | Baumann et al. ............. | 607/17 |
| 6,058,329 A | 5/2000 | Salo et al. ..................... | 607/17 |
| 6,070,100 A | 5/2000 | Bakels et al. .................. | 607/9 |
| 6,144,878 A | 11/2000 | Schroeppel et al. ........ | 600/515 |
| 6,144,880 A | 11/2000 | Ding et al. .................... | 607/23 |
| 6,208,901 B1 | 3/2001 | Hartung ....................... | 607/23 |
| 6,223,082 B1 | 4/2001 | Bakels et al. ................. | 607/17 |
| 6,280,389 B1 | 8/2001 | Ding et al. .................. | 600/485 |
| 6,371,922 B1 | 4/2002 | Baumann et al. ........... | 600/485 |
| 6,597,951 B2 | 7/2003 | Kramer et al. ................. | 607/9 |
| 2002/0143264 A1 | 10/2002 | Jiang et al. ................. | 600/510 |
| 2003/0097158 A1 | 5/2003 | Belalcazar ................... | 607/32 |
| 2003/0105496 A1 | 6/2003 | Yu et al. ....................... | 607/17 |
| 2003/0199936 A1 * | 10/2003 | Struble et al. ................ | 607/25 |

OTHER PUBLICATIONS

"Noninvasive MIKRO–TIP Pulse Pressure Transducer Model SPT–301", *Millar Instruments, Inc., Product Information*, (2000), 1 pg.

(Continued)

*Primary Examiner*—Scott M. Getzow
(74) *Attorney, Agent, or Firm*—Schwegman, Lundberg, Woessner & Kluth, P.A.

(57) ABSTRACT

This document discusses cardiac rhythm management systems and methods using the MVC-to-AE time between mitral valve closure ("MVC") and aortic ejection ("AE") of the same heart contraction, sometimes referred to as the isovolumic contraction time ("ICVT"). In one example, the MVC-to-AE time is used for predicting which patients will respond to cardiac resynchronization therapy (CRT), or other therapy. In another example, the MVC-to-AE time is used as a wellness indicator. In a further example, the MVC-to-AE time is used to select or control a therapy or therapy parameter. In one example, the MVC and AE are obtained using an accelerometer signal, however, plethysmography, tonometry, or other techniques may alternatively be used.

79 Claims, 5 Drawing Sheets

OTHER PUBLICATIONS

Adolph, Robert J., et al., "Prolongation of Isovolumic Contraction Time in Left Bundle Branch Block", *American Heart Journal, 78,* (1969),585–591.

Cazeau, S., et al., "Multisite stimulation of correction of cardiac asynchrony", *Heart, 84,* (2000),579–581.

Duncan, Sr., Alison M., et al., "The Effect of Biventricular Pacing on Ejection and Filling Hemodynamics in Dilated Cardiomyopathy Patients With Activation Disturbances: The MUSTIC Study", *JACC, Abstracts Poster Session 1167–56,* (2001), 1 pg.

Hirschfeld, Stephen, et al., "The Isovolumic Contraction Time of the Left Ventricle –An Echographic Study", *Circulation, 54,* (1976),751–756.

Kass, David A., "Improved Left Ventricular Mechanics From Acute VDD Pacing in Patients with Dilated Cardiomyopathy and Ventricular Conduction Delay", *Circulation, 99(12),* (Mar. 30, 1999),1567–1573.

Kostis, J. B., "Mechanisms of heart sounds", *American Heart Journal, 89 (4),* Letter to the Editor,(Apr. 1975), 546–547.

Kramer, Andrew P., "Automatic Selection from Multiple Cardiac Optimization Protocols",*Appl. Ser. No. 10/624,458, Filing Date: Jul. 21, 2003 Attorney Docket No. 279.340US3,* 49.

Leonelli, F. M., et al., "Systolic and Diastolic Effects of Variable Atrioventricular Delay in Patients With Complete Heart Block and Normal Ventricular Function", *The American Journal of Cardiology, 80(3),* (Aug. 1997),294–298.

Little, William C., "The Left Ventricular dP/dtmax–End–Diastolic vol. Relation in Closed–Chest Dogs", *Circulation Research, 56,* (1985),808–815.

Ritter, P., et al., "A Built–In System Based on the Peak Endocardial Acceleration (PEA) for AV–Delay Optimization In DDDR Pacing", *Pace —Pacing and Clinical Electrophysiology, No. 5,* Futura Publishing Company, Inc.,(May 1997), 1567.

Ritter, P., et al., "Determination of the optimal atrioventricular delay in DDD pacing. Comparison between echo and peak endocardial acceleration measurements", *Europace,* 1(2), (Apr. 1999),126–130.

Ritter, P., et al., "New Method for Determining the Optimal Atrio–Ventricular Delay in Patients Paces in DDD Mode for Complete Atrio–Ventricular Block", *Pace, 18, Abstract No. 237,* (Apr. 1995),855.

Spodick, D. H., et al., "Isovolumetric contraction period of the left ventricle Results in a normal series and comparsion of methods of calculation by atraumatic techniques", *American Heart Journal, 76(4),* (Oct. 1968),498–503.

Tei, C., et al., "New index of combined systolic and diastolic myocardial performance: a simple and reproducible measure of cardiac function—a study in normals and dilated cardiomyopathy", *Journal of Cardiology, 26(6),* (Dec. 1995), 357–66.

Waider, W., et al., "First heart sound and ejection sounds. Echocardiographic and phonocardiographic correlation with valvular events", *The American Journal of Cardiology,* 35(3), (Mar. 1975),346–356.

Weissler, A. M., "Systolic Time Intervals in Heart Failure in Man", *Circulation,* 37, (1968),149–159.

\* cited by examiner

CARDIAC RHYTHM MANAGEMENT SYSTEM AND METHOD USING TIME BETWEEN MITRAL VALVE CLOSURE AND AORTIC EJECTION

TECHNICAL FIELD

This document relates generally to medical systems, devices, and methods, and particularly, but not by way of limitation, to a cardiac rhythm management system using a time between a mitral valve closure and an aortic ejection, such as for prediction, diagnosis, and/or treatment.

BACKGROUND

When functioning properly, the human heart maintains its own intrinsic rhythm. Its sinoatrial node generates intrinsic electrical cardiac signals that depolarize the atria, causing atrial heart contractions. Its atrioventricular node then passes the intrinsic cardiac signal to depolarize the ventricles, causing ventricular heart contractions. These intrinsic cardiac signals can be sensed on a surface electrocardiogram (ECG) obtained from electrodes placed on the patient's skin, or from electrodes implanted within the patient's body. The surface ECG waveform, for example, includes artifacts associated with atrial depolarizations ("P-waves") and those associated with ventricular depolarizations ("QRS complexes").

A normal heart is capable of pumping adequate blood throughout the body's circulatory system. However, some people have irregular cardiac rhythms, referred to as cardiac arrhythmias. Moreover, some patients have poorly spatially-coordinated heart contractions. In either case, diminished blood circulation may result. For such patients, a cardiac rhythm management system may be used to improve the rhythm and/or spatial coordination of heart contractions. Such systems are often implanted in the patient and deliver therapy to the heart.

Cardiac rhythm management systems include, among other things, pacemakers, also referred to as pacers. Pacers deliver timed sequences of low energy electrical stimuli, called pace pulses, to the heart, such as via an intravascular lead wire or catheter (referred to as a "lead") having one or more electrodes disposed in or about the heart. Heart contractions are initiated in response to such pace pulses (this is referred to as "capturing" the heart). By properly timing the delivery of pace pulses, the heart can be induced to contract in proper rhythm, greatly improving its efficiency as a pump. Pacers are often used to treat patients with bradyarrhythmias, that is, hearts that beat too slowly, or irregularly. Such pacers may also coordinate atrial and ventricular contractions to improve pumping efficiency.

Cardiac rhythm management systems also include cardiac resynchronization therapy (CRT) devices for coordinating the spatial nature of heart depolarizations for improving pumping efficiency. For example, a CRT device may deliver appropriately timed pace pulses to different locations of the same heart chamber to better coordinate the contraction of that heart chamber, or the CRT device may deliver appropriately timed pace pulses to different heart chambers to improve the manner in which these different heart chambers contract together.

Cardiac rhythm management systems also include defibrillators that are capable of delivering higher energy electrical stimuli to the heart. Such defibrillators include cardioverters, which synchronize the delivery of such stimuli to sensed intrinsic heart activity signals. Defibrillators are often used to treat patients with tachyarrhythmias, that is, hearts that beat too quickly. Such too-fast heart rhythms also cause diminished blood circulation because the heart isn't allowed sufficient time to fill with blood before contracting to expel the blood. Such pumping by the heart is inefficient. A defibrillator is capable of delivering a high energy electrical stimulus that is sometimes referred to as a defibrillation countershock, also referred to simply as a "shock." The countershock interrupts the tachyarrhythmia, allowing the heart to reestablish a normal rhythm for the efficient pumping of blood. In addition to pacers, CRT devices, and defibrillators, cardiac rhythm management systems also include devices that combine these functions, as well as monitors, drug delivery devices, and any other implantable or external systems or devices for diagnosing or treating the heart.

One problem presented by some cardiac patients is predicting which patients will likely benefit from cardiac resynchronization therapy (e.g., left ventricular pacing, bi-ventricular pacing, and/or multisite pacing within the same heart chamber). Needlessly applying CRT pacing pulses in a patient that will not benefit from such therapy may waste energy, reducing the longevity of an implanted CRM device. Moreover, delivering CRT therapy may involve implanting additional electrodes, which may increase a patient's cost and risks. Another problem presented by some cardiac patients is determining which patients are actually benefitting from the CRT or other therapy that they are receiving. Yet another problem presented by some cardiac patients is determining whether a particular CRT or other therapy benefits a particular patient more or less than another different CRT or other therapy. For these and other reasons, the present inventors have recognized that there exists an unmet need for a predictor and/or indicator of patient wellness and/or the efficacy of CRT or other therapy.

BRIEF DESCRIPTION OF THE DRAWINGS

In the drawings, which are offered by way of example, and not by way of limitation, and which are not necessarily drawn to scale, like numerals describe substantially similar components throughout the several views. Like numerals having different letter suffixes represent different instances of substantially similar components.

SUMMARY

Figure 1:
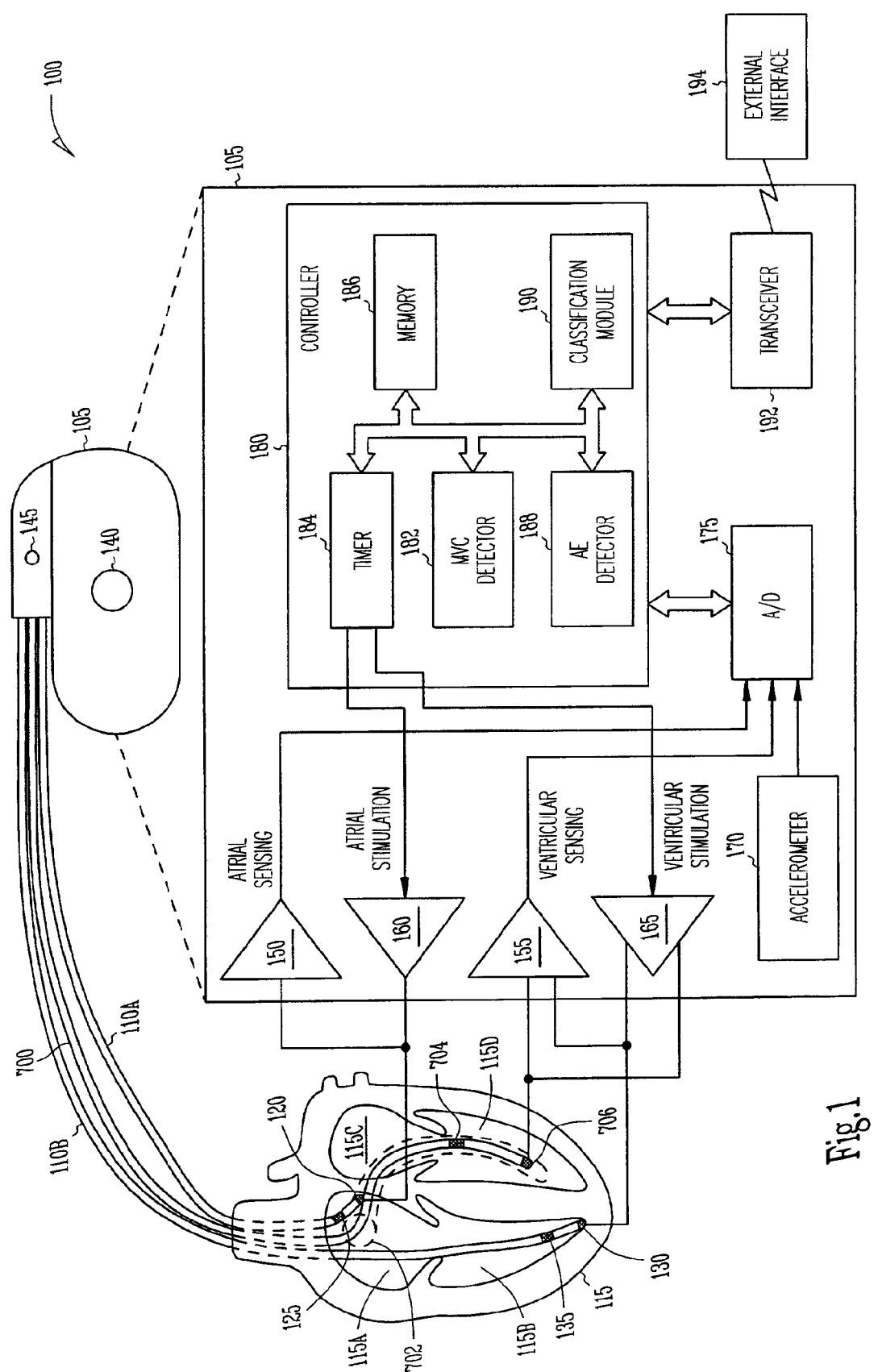
FIG. 1 is a schematic/block diagram illustrating generally one example of portions of the present cardiac rhythm management system and an environment in which it is used.

This document discusses, among other things, cardiac rhythm management systems and methods using the MVC-to-AE time between mitral valve closure ("MVC") and aortic ejection ("AE") of the same heart contraction, sometimes referred to as the isovolumic contraction time ("ICVT"). In one example, the MVC-to-AE time is used for predicting which patients will respond to cardiac resynchronization therapy (CRT), or other therapy. In another example, the MVC-to-AE time is used as a wellness indicator. In a further example, the MVC-to-AE time is used to select or control a therapy or therapy parameter. In one example, the MVC and AE are obtained using an accelerometer signal, however, plethysmography, tonometry, or other techniques may alternatively be used.

In one example, this document discusses, among other things, a system including an accelerometer, a mitral valve closure (MVC) detector circuit, an aortic ejection detector circuit, a timer, and a classification module. The accelerometer is configured to detect an acceleration signal in a subject. The MVC detector circuit is coupled to the accelerometer to receive the acceleration signal. The MVC detector circuit is configured to detect an MVC indication using information from the acceleration signal. The AE detector circuit is configured to detect an AE indication. The timer is coupled to the MVC detector circuit and the AE detector circuit. The timer is configured to measure a time interval between the MVC indication and the AE indication. The classification module is coupled to the timer to receive the measured time interval. The classification module is configured to classify the subject based on the measured time interval.

In another example, this document discusses, among other things, a method including detecting in a subject an accelerometer-based mitral valve closure (MVC) indication, detecting an aortic ejection (AE) indication, measuring a time interval between the MVC indication and the AE indication, and classifying the subject based on the measured time interval.

In another example, this document discusses, among other things, a system including an accelerometer, an MVC detector circuit, an AE detector circuit, a timer, and a wellness indicator module. The accelerometer is configured to detect an acceleration signal in a subject. The MVC detector circuit is coupled to the accelerometer to receive the acceleration signal, and is configured to detect an MVC indication using information from the acceleration signal. The AE detector circuit is configured to detect an AE indication. The timer is coupled to the MVC detector circuit and the AE detector circuit. The timer is configured to measure a time interval between the MVC indication and the AE indication. The wellness indicator module is coupled to the timer to receive the measured time interval, and is configured to compute a wellness indication of the subject based on the measured time interval.

In another example, this document discusses, among other things, a method including detecting in a subject an accelerometer-based mitral valve closure (MVC) indication, detecting an aortic ejection (AE) indication, measuring a time interval between the MVC indication and the AE indication, and computing a wellness indication of the subject based on the measured time interval. Other aspects of the discussed systems, methods, and apparatuses will become apparent upon reading the following detailed description and viewing the drawings that form a part thereof.

DETAILED DESCRIPTION

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized and that structural, logical and electrical changes may be made without departing from the spirit and scope of the present invention. The following detailed description is, therefore, not to be taken in a limiting sense, and the scope of the present invention is defined by the appended claims and their equivalents.

This document discusses systems and methods using a time interval from mitral valve closure to aortic ejection. These systems and methods will be described in applications involving implantable medical devices including, but not limited to, implantable cardiac rhythm management systems such as pacemakers, cardioverter/defibrillators, pacer/defibrillators, biventricular or other multi-site resynchronization or coordination devices, and drug delivery systems. However, these systems and methods may be employed in unimplanted devices, including, but not limited to, external pacemakers, cardioverter/defibrillators, pacer/defibrillators, biventricular or other multi-site resynchronization or coordination devices, monitors, programmers and recorders, whether such devices are used for providing a diagnostic, a therapy, or both a diagnostic and a therapy.

FIG. 1 is a schematic/block diagram illustrating generally one example of portions of the present cardiac rhythm management system 100 and an environment in which it is used. In this example, system 100 includes, among other things, cardiac rhythm management device 105, which is coupled by leads 110A–B to heart 115. In this illustrative example, lead 110A is introduced into a right atrium, lead 110B is introduced into the right ventricle, and lead 700 is introduced through coronary sinus 702 such that electrodes 704 and 706 are communicatively coupled to a left ventricle portion of heart 115.

In one example device 105 also includes an accelerometer 170, such as within the housing of device 105, which is pectorally or abdominally implanted close enough to heart 115 to sense acceleration from heart contractions. Accelerometer 170 outputs a heart acceleration signal to analog-to-digital ("A/D") converter 175, for conversion into a digitized signal. A/D converter is coupled to controller 180 to provide the digitized acceleration signal to controller 180.

Controller 180 is capable of sequencing through various control states such as, for example, by using a digital microprocessor having executable instructions stored in an associated instruction memory circuit, a microsequencer, or a state machine. In operation, by execution of these instructions, controller 180 implements a mitral valve closure ("MVC") detector circuit 182, a timer 184, a memory 186, and an aortic ejection ("AE") detection circuit 188. In one example, MVC detector 182 is coupled to accelerometer 170 through A/D converter 175 such that it receives the digitized heart acceleration signal. Using this digitized heart acceleration signal, MVC detector 182 detects mitral valve closure of heart 115. The corresponding time of this event is input to timer 184. In one example, AE detector 188 is coupled to accelerometer 170 through A/D converter 175 such that it receives the digitized heart acceleration signal. Using this digitized heart acceleration signal, AE detector 188 detects aortic ejection of blood flow. The corresponding time of this event is input to timer 184.

Timer 184 measures the time of MVC to the later time of the corresponding AE of the same heart contraction. This time is referred to as the MVC-to-AE interval and is sometimes called the isovolumic contraction time ("IVCT") interval. Classification module 190 is coupled to the timer 184 and receives the measured MVC-to-AE interval. In one example, the classification module 190 includes a comparator that compares the measured MVC-to-AE interval against a predetermined interval or range of intervals, such as a a normal or control range of intervals, to predict whether or how the subject will respond to CRT. In one example, the subject is deemed a likely responder to CRT if the MVC-to-AE interval exceeds a predetermined threshold value. In this example the threshold is selected between about 50 milliseconds and about 80 milliseconds, such as about 78 milliseconds, by way of example, but not by way of limitation. In another example, the classification module 190 includes a difference circuit. One input of the difference circuit receives a predetermined threshold value for the MVC-to-AE interval. The second input to the difference circuit receives the measured MVC-to-AE interval. The difference circuit subtracts the predetermined threshold from the measured MVC-to-AE interval to output an indication of a degree to which the subject is likely to respond to CRT. In a further example, the measured MVC-to-AE interval, or an indication of whether the threshold value was exceeded, is provided to transceiver 192, which is coupled to controller 180, and transmitted to external interface 194, such as for display to a physician or other user, such as on a computer monitor, printout, or other data output mechanism.

Figure 2:
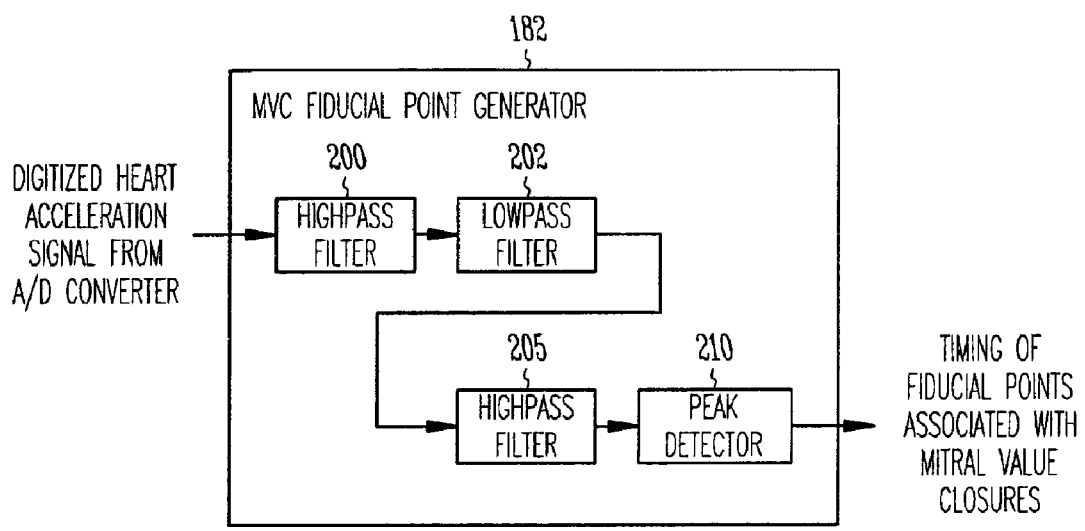
FIG. 2 is a schematic/block diagram illustrating generally one example of portions of an MVC detector.

FIG. 2 is a schematic/block diagram illustrating generally one example of portions of MVC detector 182. In this example, MVC detector 182 includes a highpass filter 200, a lowpass filter 202, a highpass filter 205, and a peak detector 210, although it is understood that certain of these components could be combined rather than implemented separately (e.g., a highpass and lowpass filter could be combined into a bandpass filter, etc.). In one example, highpass filter 200 receives the digitized heart acceleration signal from A/D converter 175, removes baseline (i.e., constant or low frequency drift) signal components, and provides a resulting output signal to an input of lowpass filter 202. In this example, lowpass filter 202 is a 5-sample moving average "boxcar" filter attenuating signal frequencies above approximately 100 Hz. Lowpass filter 202 receives the baseline-filtered heart acceleration signal from highpass filter 200, and outputs a resulting lowpass filtered heart acceleration signal to an input of highpass filter 205. In one example, highpass filter 205 is a differentiator that takes a first derivative of its input lowpass filtered heart acceleration signal, received from the output of lowpass filter 202, and outputs a resulting first derivative heart acceleration signal to an input of peak detector 210. In one example, peak detector 210 detects negative peaks of the first derivative heart acceleration signal. However, it is understood that a polarity reversal of accelerometer 170 and/or signal inversion(s) in the signal processing path of the heart acceleration signal may alternatively use a detection of positive peaks of the first derivative heart acceleration signal. For each cycle of heart contraction and heart relaxation ("cardiac cycle"), the first negative peak of the first derivative heart acceleration signal occurring after an intrinsic or paced ventricular depolarization and before the next intrinsic or paced atrial depolarization is deemed an MVC fiducial point associated with the mitral valve closure. An indication of the time at which such MVC fiducial points occur is provided by MVC detector 182 to timer 184 for calculation of the corresponding MVC-to-AE time interval discussed above.

In one example, AE detector 188, includes a matched filter to detect the AE from the digitized acceleration signal. One example of a matched filter is described in Carlson U.S. Pat. No. 5,674,256, CARDIAC PRE-EJECTION PERIOD DETECTION, which is assigned to Cardiac Pacemakers, Inc., and which is incorporated by reference herein in its entirety, including its description of a matched filter. In this example, a predetermined model accelerometer signal, including AE fiducial information, evaluated during baseline conditions is obtained from a patient or population. The model signal segment is used as a template during an auto-regression ("AR") comparison. In one example, the segment's starting and ending points are defined with respect to ECG fiducial points and/or accelerometer fiducial points such as MVC. The AR compares the accelerometer signal obtained from the subject to the AE fiducial information of the model signal segment. The AR yields a statistical figure of merit that is evaluated to provide the AE time.

Figure 3:
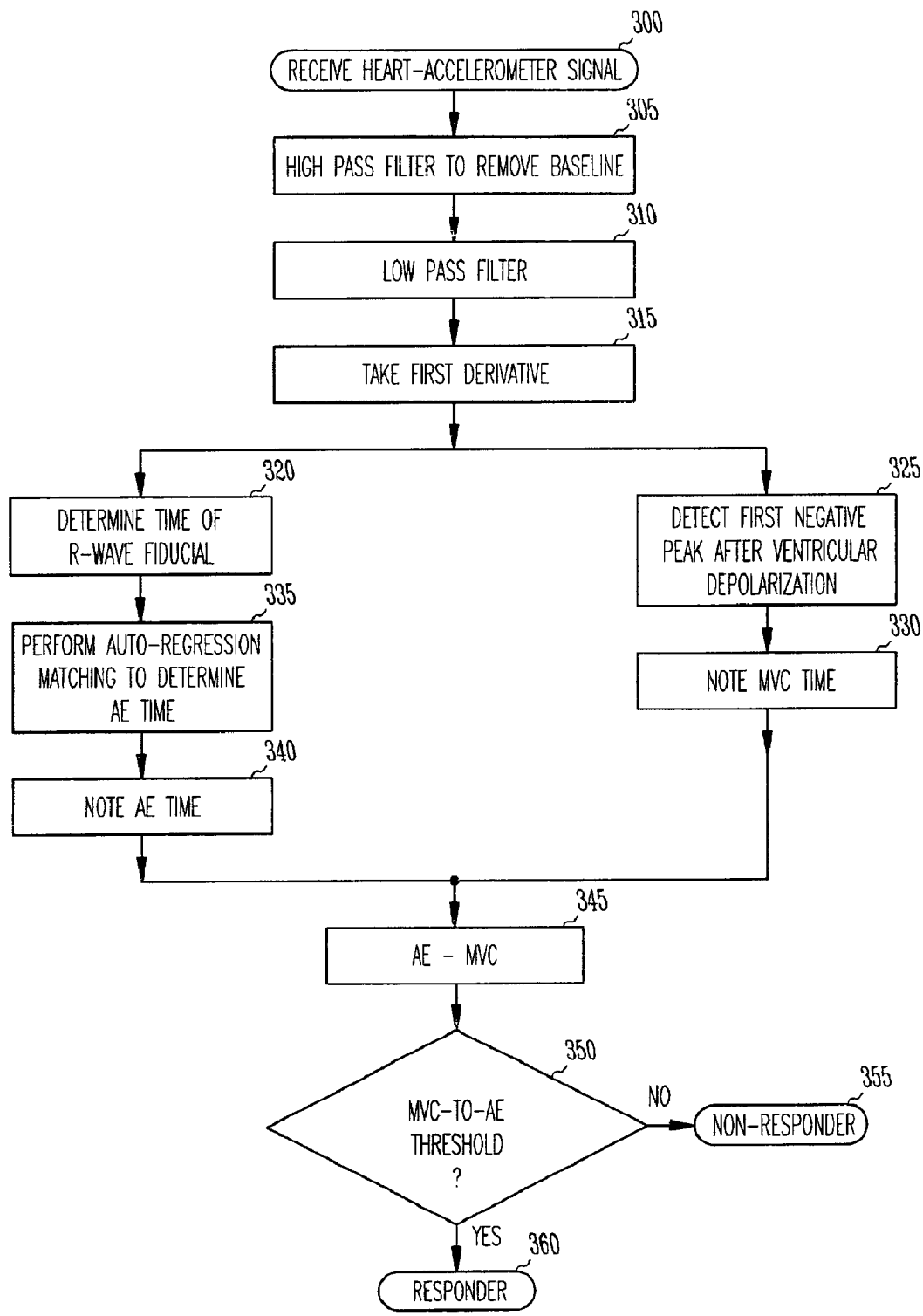
FIG. 3 is a flow chart illustrating generally one example of a technique for determining whether a particular subject will likely respond to CRT.

FIG. 3 is a flow chart illustrating generally one example of a technique for determining whether a particular subject will likely respond to CRT (i.e., subject is deemed a likely responder). At 300, the accelerometer signal is received. At 305, the baseline dc or low frequency component of the acceleration signal is removed by highpass filtering. At 310, the heart acceleration signal is lowpass filtered. At 315, the lowpass filtered heart acceleration signal is differentiated to obtain a resulting first derivative heart acceleration signal. Then, operations are carried out for obtaining the MVC and AE times; some of these operations may be carried out substantially concurrently.

Figure 4:
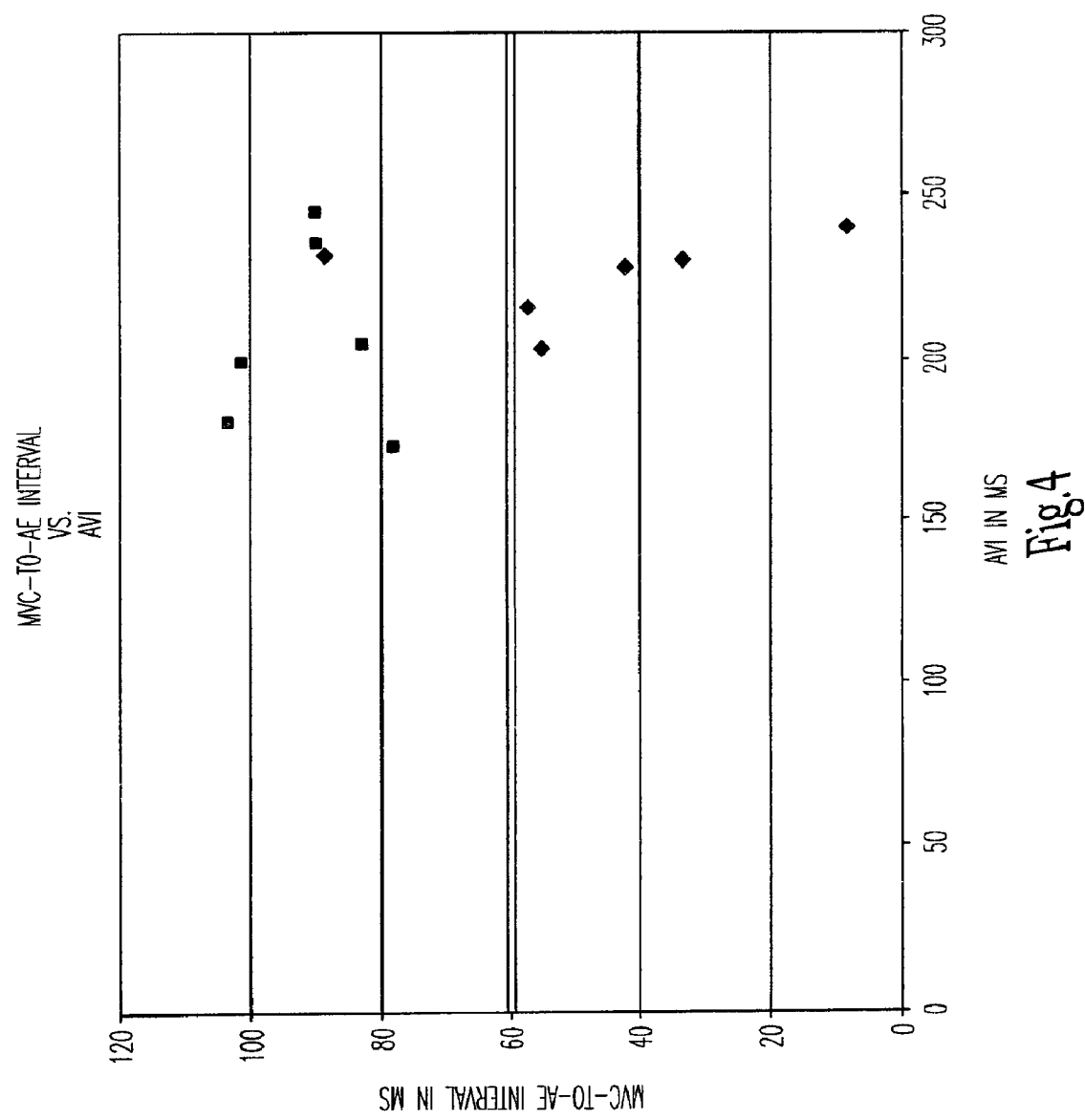
FIG. 4 is a graph of patient data illustrating generally one example of MVC-to-AE intervals versus Atrial—Ventricular Interval ("AVI").

At 320, the time of a fiducial associated with an intrinsic or paced ventricular depolarization is determined. At 325, a first positive or negative peak of the first derivative heart acceleration signal (i.e., in this case, a first negative peak occurring after the intrinsic or paced ventricular depolarization and before a next intrinsic or paced atrial depolarization) is detected and deemed a fiducial point associated with mitral valve closure for that cardiac cycle. At 330, the MVC time is noted. In this example, at 335, the aortic ejection (AE) time is determined by auto-regression matching of a segment of the accelerometer signal (occurring after the R-wave fiducial is detected at 320) to a predetermined model or template, such as by using the matched filter technique described in Carlson (U.S. Pat. No. 5,674,256). The time of the AE is noted at 340. At 345, the difference between the times of the AE and MVC events is calculated, yielding an MVC-to-AE time interval. If, at 350, the MVC-to-AE time interval exceeds the predetermined threshold value, the subject is classified as a responder at 360. If the threshold value exceeds the MVC-to-AE time interval, the subject is classified as a non-responder at 355. The case where the MVC-to-AE time equals the threshold value can be arbitrarily assigned to either the responder or non-responder classification. FIG. 4 is a graph of patient data illustrating generally one example of MVC-to-AE intervals versus Atrial-Ventricular Interval ("AVI"). In this example, a threshold value of 60 ms was used to effectively separate responders and non-responders. However, another threshold value may also be used, as discussed above.

In an alternate example, the MVC-to-AE time interval is used in conjunction with another indicator to classify a patient as a responder or non-responder. In one example, if a patient's MVC-to-AE interval exceeds a first predetermined threshold (e.g., 60 ms) and the patient's QRS width (i.e., the duration of the QRS complex measured from a lead electrode, or otherwise) exceeds a second predetermined threshold (e.g., 155 ms, for one example of a QRS complex obtained from surface ECG electrode; a different value may be appropriate for a QRS complex obtained from an intracardiac electrogram electrode), the patient is classified as a responder and/or further classified as a "robust" responder. In one example, the QRS width is measured from at least one cardiac signal received from at least one lead electrode, using one or more level detectors, to detect the beginning and end of the QRS complex, and a timer to measure the time difference between the measured beginning and end of the QRS complex.

Figure 5:
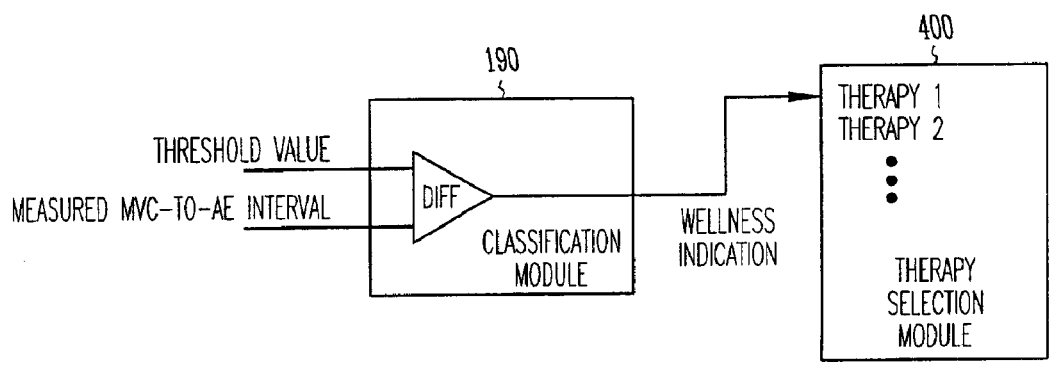
FIG. 5 is a block diagram illustrating generally one example of how the value of the MVC-to-AE interval is used as a wellness and/or therapy efficacy indicator, and/or to adjust therapy to increase efficacy and/or wellness.

FIG. 5 is a block diagram illustrating generally one example of how the value of the MVC-to-AE interval is used as a contractility indicator, a wellness indicator; and/or therapy efficacy indicator, and/or to adjust therapy to increase efficacy and/or contractility or wellness. In this example, the output of a comparator or other difference circuit in the classification (and/or wellness indicator) module 190 indicates a difference between the measured MVC-to-AE interval and a threshold value. In one example, the threshold value is the threshold for responder/non-responder classification discussed above. In another example, the threshold value is an MVC-to-AE interval chosen from the normal or control range of intervals. In this example the threshold is selected between about 30 milliseconds and about 50 milliseconds, such as about 40 milliseconds, by way of example, but not by way of limitation. This indication may vary over a plurality of cardiac cycles, and is therefore used as a wellness indicator. Alternatively, the wellness indicator may be the measured MVC-to-AE interval obtained over a plurality of cardiac cycles. The wellness indicator indicates greater wellness for a shorter measured MVC-to-AE interval than for a longer measured MVC-to-AE interval. The wellness indicator can be averaged and can also be used to indicate therapy efficacy for the cardiac rhythm management being provided. In one example, the wellness indicator is used to compare the efficacy of particular therapies (e.g. Therapy 1, Therapy 2, . . . Therapy N) for selecting and using a therapy that the wellness indicator deems relatively more effective. In another example, the wellness indicator is used to evaluate the efficacy of a single therapy having a variable parameter (e.g., DDD pacing with variable AV delay) so that a particular value of the therapy parameter (e.g., AV delay, pacing electrode selection, interventricular delay, etc.) can be selected to obtain a higher degree of wellness. In another example, the wellness indicator is used by a therapy selection module 400 to determine or control a specific therapy, or therapy parameter (e.g., AV delay, pacing electrode selection, interventricular delay, etc.), for the cardiac rhythm management being provided.

One example of controlling a therapy uses cardiac resynchronization therapy (CRT) delivering appropriately timed pace pulses to multiple sites in one or more heart chambers to better coordinate the spatial nature of the heart contraction. One such example couples heart chamber stimulation circuit 165 to multiple electrode lead 700 in FIG. 1. Another possible example of the therapy delivers appropriately timed pace pulses to different heart chambers to improve the manner in which these different heart chambers contract together. One such example includes multiple electrode leads 700 and 110 in FIG. 1 coupled to heart chamber stimulation circuits 165 and 160. In this example, therapy module 400 determines whether CRT is needed and determines the timing of the pulses delivered to the electrodes.

Although certain examples of the system and its operation have been described above using a signal from an implanted accelerometer to determine the time of MVC, and an acceleration-based AR comparison to determine the time of AE, it is understood that other embodiments of the system may obtain these measurements differently. One example uses an accelerometer signal generated from an accelerometer temporarily mounted on the patient's chest to detect MVC. Another example detects AE by non-invasively monitoring the carotid arterial-pulse or by using a catheter to invasively monitor aortic pressure, such as in the ascending portion of the aorta. An example of non-invasively monitoring uses plethysmography (recording changes of the size of a part as modified by the circulation of blood in it, for example, using a finger cuff and infrared light measurement) or tonometry (measurement of tension or pressure, for example, at the carotid artery).

It is to be understood that the above description is intended to be illustrative, and not restrictive. For example, the above-discussed examples may be used in combination with each other. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, the terms "first," "second," "third," etc. are used merely as labels, and are not intended to impose numeric requirements on their objects.

What is claimed is:

1. A system including:
   an accelerometer, configured to detect an acceleration signal in a subject;
   a mitral valve closure (MVC) detector circuit, coupled to the accelerometer to receive the acceleration signal, and configured to detect an MVC indication using information from the acceleration signal;
   an aortic ejection (AE) detector circuit, configured to detect an AE indication;
   a timer, coupled to the MVC detector circuit and the AE detector circuit, the timer configured to measure a time interval between the MVC indication and the AE indication; and
   a classification module, coupled to the timer to receive the measured time interval, and configured to classify the subject based on the measured time interval.

2. The system of claim 1, in which the classification module includes a comparator, the comparator including a first input to receive the measured time interval, a second input to receive a predetermined threshold time interval, and a comparator output to indicate whether the measured time interval exceeds the threshold time interval.

3. The system of claim 2, in which the threshold time interval is between about 50 milliseconds and about 80 milliseconds.

4. The system of claim 3, in which the threshold time interval is about 78 milliseconds.

5. The system of claim 3, in which the threshold time interval is about 60 milliseconds.

6. The system of claim 2, in which the classification module is configured to classify the subject as a likely responder to cardiac resynchronization therapy (CRT) if the comparator output indicates that the measured time interval exceeds the threshold time interval.

7. The system of claim 2, in which the classification module is configured to classify the subject as a likely non-responder to cardiac resynchronization therapy (CRT) if the comparator output indicates that the threshold time interval exceeds the measured time interval.

8. The system of claim 1, in which the classification module includes an indication, based on the measured time interval, that predicts a degree to which the subject is likely to respond to a particular therapy.

9. The system of claim 8, in which the classification module includes an indication, based on the measured time interval, that predicts a degree to which the subject is likely to respond to cardiac resynchronization therapy.

10. The system of claim 1, further including a highpass filter circuit, including an input coupled to receive the acceleration signal from the accelerometer, and an output providing a highpass-filtered acceleration signal.

11. The system of claim 10, in which the highpass filter circuit includes a differentiator circuit.

12. The system of claim 10, further including a lowpass filter circuit, including an input coupled to the output of the highpass filter to receive the highpass-filtered acceleration signal, and including an output providing a bandpass-filtered acceleration signal.

13. The system of claim 10, further including a peak/level detector configured to detect at least one of a positive or negative peak or level of the highpass-filtered acceleration signal to obtain the MVC indication.

14. The system of claim 13, further including:
   an R-wave detector circuit, configured to detect in the subject an intrinsic heart signal associated with a ventricular contraction;
   a P-wave detector circuit, configured to detect in the subject an intrinsic heart signal associated with an atrial contraction occurring after the detected ventricular contraction; and
   in which the peak/level detector is configured to obtain the MVC indication by detecting a peak or level of the highpass-filtered acceleration signal that occurs after the R-wave and before the P-wave.

15. The system of claim 1, in which the AE detector circuit includes an autoregression module configured to compare a portion of the acceleration signal to a model signal, obtained from the subject, to detect the AE indication.

16. The system of claim 1, in which the AE detector circuit includes at least one of:
   a pressure transducer, adapted to detect an end-diastolic aortic blood pressure associated with the AE indication and an onset of aortic flow; and
   a plethysmograph adapted to detect the AE indication.

17. The system of claim 1, further including:
   an electrode, configured to receive a cardiac signal;
   at least one level detector, coupled to the electrode and configured to detect a beginning and end of a QRS complex; and
   a timer, coupled to the at least one level detector and configured to measure a QRS width time duration.

18. A method including:
   detecting in a subject an accelerometer-based mitral valve closure (MVC) indication;
   detecting an aortic ejection (AE) indication;
   measuring a time interval between the MVC indication and the AE indication; and
   classifying the subject based on the measured time interval.

19. The method of claim 18, in which the classifying includes comparing the measured time interval to a predetermined threshold time interval.

20. The method of claim 19, in which the threshold time interval is between about 50 milliseconds and about 80 milliseconds.

21. The method of claim 20, in which the threshold time interval is about 78 milliseconds.

22. The method of claim 20, in which the threshold time interval is about 60 milliseconds.

23. The method of claim 19, in which the classifying further includes:
   classifying the subject into a first class if the measured time interval exceeds the threshold time interval; and
   classifying the subject into a second class if the threshold time interval exceeds the measured time interval.

24. The method of claim 23, in which the classifying the subject into a first class includes classifying the subject as a likely responder to cardiac resynchronization therapy (CRT).

25. The method of claim 23, in which the classifying the subject into a second class includes classifying the subject as a likely non-responder to cardiac resynchronization therapy (CRT).

26. The method of claim 18, in which the classifying the subject based on the measured time interval includes providing a therapy responsiveness prediction indicating a higher likelihood of responsiveness for larger values of the measured time interval than the likelihood of responsiveness for smaller values of the measured time interval.

27. The method of claim 26, in which the providing the therapy responsiveness prediction includes predicting a likelihood that the subject will benefit from cardiac resynchronization therapy.

28. The method of claim 18, in which detecting the MVC indication includes:
   detecting an acceleration signal; and
   highpass filtering the acceleration signal to form a highpass-filtered acceleration signal.

29. The method of claim 28, in which highpass filtering the acceleration signal includes at least one of:
   (1) removing a baseline component of the acceleration signal; and
   (2) differentiating the acceleration signal.

30. The method of claim 29, further including lowpass filtering the acceleration signal.

31. The method of claim 30, further including detecting at least one of a positive or negative peak of the highpass-filtered acceleration signal to obtain the MVC indication.

32. The method of claim 31, further including detecting a negative peak of the highpass filtered acceleration signal to obtain the MVC indication.

33. The method of claim 31, including:
   detecting in the subject an R-wave associated with a ventricular contraction;
   detecting in the subject a P-wave associated with an atrial contraction occurring after the detected ventricular contraction; and
   detecting from the highpass-filtered acceleration signal at least one of a positive or negative peak that occurs after the R-wave and before the P-wave to obtain the MVC indication.

34. The method of claim 31, including:
   lowpass filtering the highpass-filtered acceleration signal to obtain a bandpass filtered acceleration signal;
   detecting in the subject an R-wave associated with a ventricular contraction;
   detecting in the subject a P-wave associated with an atrial contraction occurring after the detected ventricular contraction; and
   detecting, from a signal based on the bandpass filtered acceleration signal, at least one of a positive or negative peak that occurs after the R-wave and before the P-wave to obtain the MVC indication.

35. The method of claim 18, in which the detecting the AE indication includes comparing a portion of an acceleration-based signal to a model signal obtained from the subject.

36. The method of claim 35, in which the comparing is performed autoregressively.

37. The method of claim 36, in which the comparing is confined to a predetermined time window referenced at least in part to an intrinsic heart signal obtained from the subject.

38. The method of claim 18, in which detecting the AE indication includes at least one of:
   detecting an aortic pressure at end-diastole and onset of aortic flow;
   detecting an acceleration associated with the aortic pressure end-diastole and an onset of aortic flow; and
   detecting at least one of a plethysmographic indication and a tonometric indication associated with the aortic pressure end-diastole and onset of aortic flow.

39. The method of claim 38, in which the detecting the at least one of the plethysmographic indication and tonometric indication uses at least one of a finger location and a carotid location, respectively.

40. The method of claim 18, further including detecting a QRS complex and measuring a time duration of the QRS complex, and in which the classifying the subject is also based on the measured QRS width.

41. A system including:
   an accelerometer, configured to detect an acceleration signal in a subject;
   a mitral valve closure (MVC) detector circuit, coupled to the accelerometer to receive the acceleration signal, and configured to detect an MVC indication using information from the acceleration signal;
   an aortic ejection (AE) detector circuit, configured to detect an AE indication;
   a timer, coupled to the MVC detector circuit and the AE detector circuit, the timer configured to measure a time interval between the MVC indication and the AE indication; and
   a wellness indicator module, coupled to the timer to receive the measured time interval, and configured to compute a wellness indication of the subject based on the measured time interval.

42. The system of claim 41, in which the wellness indicator module includes a difference circuit, the difference circuit including a first input to receive the measured time interval, a second input to receive a predetermined threshold time interval, and a difference circuit output providing the wellness indicator indicating a degree to which the measured time interval exceeds the predetermined threshold time interval.

43. The system of claim 42, in which the threshold time interval is between about 30 milliseconds and about 50 milliseconds.

44. The system of claim 43, in which the threshold time interval is about 40 milliseconds.

45. The system of claim 41, in which the wellness indicator indicates a greater wellness for a shorter measured time interval than for a longer measured time interval.

46. The system of claim 41, further including:
   a therapy circuit, configured to provide therapy to the subject; and
   a therapy adjustment module, configured to adjust the therapy based at least in part on the wellness indicator.

47. The system of claim 46, in which therapy circuit includes a pacing pulse circuit, coupled to the subject, and in which the therapy adjustment module includes at least one of:
   an AV delay adjustment;
   an electrode selection; and
   an interventricular delay selection.

48. The method of claim 46, in which the therapy circuit includes a cardiac resynchronization therapy circuit.

49. The method of claim 46, in which the therapy circuit includes a cardiac rhythm management therapy circuit.

50. The system of claim 41, further including a highpass filter circuit, including an input coupled to receive the acceleration signal from the accelerometer, and an output providing a highpass-filtered acceleration signal.

51. The system of claim 50, in which the highpass filter circuit includes a differentiator circuit.

52. The system of claim 50, further including a lowpass filter circuit, including an input coupled to the output of the highpass filter to receive the highpass-filtered acceleration signal, and including an output providing a bandpass-filtered acceleration signal.

53. The system of claim 50, further including a peak/level detector configured to detect at least one of a positive or negative peak or level of the highpass-filtered acceleration signal to obtain the MVC indication.

54. The system of claim 53, further including:
   an R-wave detector circuit, configured to detect in the subject an intrinsic heart signal associated with a ventricular contraction;
   a P-wave detector circuit, configured to detect in the subject an intrinsic heart signal associated with an atrial contraction occurring after the detected ventricular contraction; and
   in which the peak/level detector is configured to obtain the MVC indication by detecting a peak or level of the highpass-filtered acceleration signal that occurs after the R-wave and before the P-wave.

55. The system of claim 41, in which the AE detector circuit includes an autoregression module configured to compare a portion of the acceleration signal to a model signal, obtained from the subject, to detect the AE indication.

56. The system of claim 41, in which the AE detector circuit includes at least one of a:
   pressure transducer, adapted to detect an end-diastolic aortic blood pressure associated with the AE indication;
   a plethysmograph adapted to detect the AE indication; and
   a tonometer adapted to detect the AE indication.

57. A method including:
   detecting in a subject an accelerometer-based mitral valve closure (MVC) indication;
   detecting an aortic ejection (AE) indication;
   measuring a time interval between the MVC indication and the AE indication; and
   computing a wellness indication of the subject based on the measured time interval.

58. The method of claim 57, in which the determining includes subtracting a predetermined threshold time interval from the measured time interval.

59. The method of claim 58, in which the threshold time interval is between about 30 milliseconds and about 50 milliseconds.

60. The method of claim 59, in which the threshold time interval is about 40 milliseconds.

61. The method of claim 57, in which the computing the wellness indication includes indicating a higher degree of wellness for a smaller value of the measured time interval than for a larger value of the measured time interval.

62. The method of claim 57, further including:

providing a therapy to the subject; and assessing an efficacy of the therapy based on the computed wellness indication.

63. The method of claim 62, further including adjusting the therapy based at least in part on the assessed efficacy of the therapy.

64. The method of claim 63, in which adjusting the therapy includes at least one of:

an AV delay adjustment;

an electrode selection; and an interventricular delay selection.

65. The method of claim 62, in which providing the therapy to the subject includes providing a cardiac resynchronization therapy.

66. The method of claim 62, in which providing the therapy to the subject includes providing a cardiac rhythm management therapy.

67. The method of claim 57, in which detecting the MVC indication includes:

detecting an acceleration signal; and highpass filtering the acceleration signal to form a highpass-filtered acceleration signal.

68. The method of claim 67, in which highpass filtering the acceleration signal includes at least one of:

(1) removing a baseline component of the acceleration signal; and (2) differentiating the acceleration signal.

69. The method of claim 68, further including lowpass filtering the acceleration signal.

70. The method of claim 68, further including detecting at least one of a positive or negative peak of the highpass-filtered acceleration signal to obtain the MVC indication.

71. The method of claim 70, further including detecting at least one of a positive or negative peak of the highpass filtered acceleration signal to obtain the MVC indication.

72. The method of claim 70, including:

detecting in the subject an R-wave associated with a ventricular contraction;

detecting in the subject a P-wave associated with an atrial contraction occurring after the detected ventricular contraction; and detecting from the highpass-filtered acceleration signal a peak that occurs after the R-wave and before the P-wave to obtain the MVC indication.

73. The method of claim 70, including:

lowpass filtering the highpass-filtered acceleration signal to obtain a bandpass filtered acceleration signal;

detecting in the subject an R-wave associated with a ventricular contraction;

detecting in the subject a P-wave associated with an atrial contraction occurring after the detected ventricular contraction; and detecting from a signal based on the bandpass filtered acceleration signal at least one of a positive or negative peak that occurs after the R-wave and before the P-wave to obtain the MVC indication.

74. The method of claim 57, in which the detecting the AE indication includes comparing a portion of an acceleration-based signal to a model signal obtained from the subject.

75. The method of claim 74, in which the comparing is performed autoregressively.

76. The method of claim 75, in which the comparing is confined to a predetermined time window referenced at least in part to an intrinsic heart signal obtained from the subject.

77. The method of claim 57, in which detecting the AE indication includes at least one of:

detecting an aortic pressure at end-diastole;

detecting an acceleration associated with aortic flow onset at the aortic pressure end-diastole; and detecting at least one of a plethysmographic indication and a tonometric indication associated with aortic flow onset at the aortic pressure diastole.

78. The method of claim 77, in which the detecting the plethysmographic indication uses at least one of a carotid location and a finger location.

79. The method of claim 57, in which the computing an wellness indication of the subject based on the measured time interval includes computing a contractility indication of the subject based on the measured time interval.

* * * * *